United States Patent [19]

Takase et al.

[11] Patent Number: 5,380,913
[45] Date of Patent: Jan. 10, 1995

[54] PROCESS FOR PRODUCING METHOXYIMINOACETAMIDE COMPOUNDS AND INTERMEDIATES

[75] Inventors: Akira Takase, Otsu; Hiroyuki Kai, Koriyama; Kuniyoshi Nishida, Koga; Shoji Shinomoto, Matsubara; Masahiko Nagai, Amagasaki, all of Japan

[73] Assignee: Shionogi & Co., Ltd., Osaka, Japan

[21] Appl. No.: 120,392

[22] Filed: Sep. 14, 1993

Related U.S. Application Data

[60] Continuation-in-part of Ser. No. 964,042, Oct. 21, 1992, abandoned, which is a division of Ser. No. 733,303, Jul. 22, 1991, Pat. No. 5,183,921.

[30] Foreign Application Priority Data

Jul. 26, 1990 [JP] Japan ............... 2-200696

[51] Int. Cl.⁶ ............... C07C 229/34; C07C 233/11
[52] U.S. Cl. ............... 560/35; 564/164; 564/165
[58] Field of Search ............... 560/35; 564/164, 165

[56] References Cited

U.S. PATENT DOCUMENTS

| | | | |
|---|---|---|---|
| 4,472,317 | 9/1984 | Martin | 558/301 |
| 5,183,921 | 2/1993 | Takase et al. | 558/301 |

FOREIGN PATENT DOCUMENTS

| | | | |
|---|---|---|---|
| 1131650 | 9/1982 | Canada | 558/301 |
| 0253213 | 1/1988 | European Pat. Off. | |
| 0254426 | 1/1988 | European Pat. Off. | |
| 0398692 | 11/1990 | European Pat. Off. | |

OTHER PUBLICATIONS

Methoden Der Organischen Chemie (Houben Weyl) 4th Edition, vol. X/4 1968 Georg Thieme Verlag Stuttgart pp. 282–294.

Methoden Der Organischen Chemie (Houben Weyl) 4th Edition, vol. X/4 1968 Georg Thieme Verlag Stuttgart pp. 220–223.

*Primary Examiner*—Joseph Paul Brust
*Attorney, Agent, or Firm*—Wenderoth, Lind & Ponack

[57] ABSTRACT

A compound of the formula [I]:

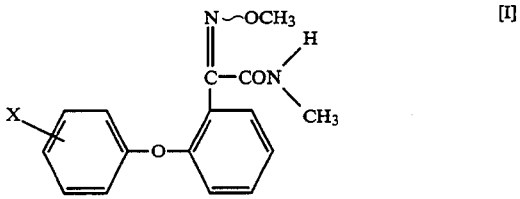

wherein X is hydrogen, lower alkyl, lower alkoxy or halogen; ~ is any configuration of E-isomer, Z-isomer or a mixture thereof is produced by reacting a compound of the formula [II]

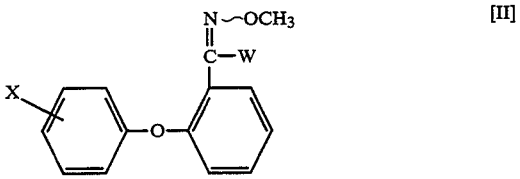

wherein X and ~ are as defined above; W is —CN or —COOR; and R is a lower alkyl, with methylamine in the presence of methanol. The compound [I] is useful for an agricultural fungicide. An intermediate used for producing the compound [I] is also disclosed.

3 Claims, No Drawings

PROCESS FOR PRODUCING METHOXYIMINOACETAMIDE COMPOUNDS AND INTERMEDIATES

This application is a continuation-in-part application of application Ser. No. 07/964,042 filed Oct. 21, 1992, now abandoned, which is a division of application Ser. No. 07/733,303 filed Jul. 22, 1991 now U.S. Pat. No. 5,183,921.

FIELD OF THE INVENTION

The present invention relates to a process for producing methoxyiminoacetamide compounds of the formula:

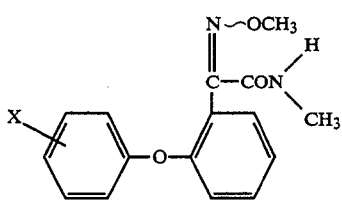

wherein X is hydrogen, lower alkyl, lower alkoxy or halogen; and — is any configuration of E-isomer, Z-isomer or a mixture thereof, which are useful as agricultural fungicides, and intermediates used for the production of the compounds of the formula [I].

BACKGROUND OF THE INVENTION

The compounds of the formula [I] are novel compounds which have been disclosed for the first time in EP-A-398 692 in the name of the present assignee, and they are considered to be remarkably useful compounds as agricultural fungicides having excellent fungicidal activities against microorganisms such as *Piricularia oryzae*, *Pellicularia sasakii*, *PseudoperonosDora cubensis* and the like.

In the above application, the compounds of the formula [I] are produced by several routes. However, at this time, the present inventors have found other novel synthetic routes for producing the compounds of the formula [I] which are more economical with minimum by-products.

OBJECTS OF THE INVENTION

One object of the present invention is to provide a novel process for producing the methoxyiminoacetamide compounds of the formula [I] which are useful for agricultural fungicides.

Another object of the present invention is to provide a novel intermediate used in the process of the present invention.

These objects as well as other objects and advantages of the present invention will become apparent to those skilled in the art from the following description.

SUMMARY OF THE INVENTION

According to the present invention, the compound of the above formula [I] is produced by reacting a compound of the formula [II]:

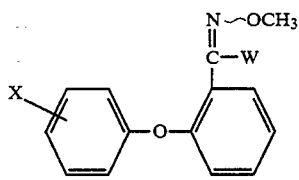

wherein X and — are as defined above; W is —CN or —COOR; and R is lower alkyl, with methylamine in the presence of methanol. The compound of the formula [II] is produced by methylating a compound of the formula [III]:

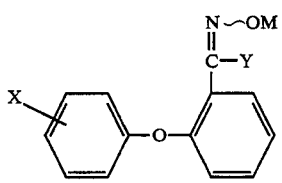

wherein X, R and — are as defined above; Y is —CN, —COOH or —COOR; and M is hydrogen or an alkali metal, with a compound of the formula:

 [IV]

wherein L is halogen or —OSO₂OCH₃.

Alternatively, the compound of the formula [I] is produced by methylating a compound of the formula [IV]:

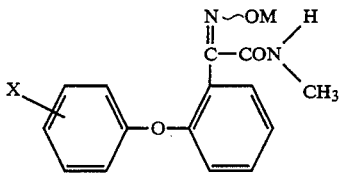

wherein X, M and — are as defined above with a compound of the formula:

 [IV]

wherein L is halogen or —OSO₂OCH₃.

Among the compounds of the formula [II], the compounds wherein Z is —CN, i.e., the compounds of the formula [II']:

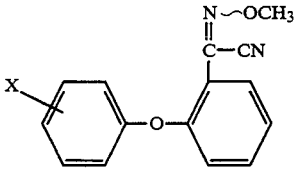

wherein X and — are as defined above, have not been disclosed heretofore in the prior art and are novel compounds. Thus, the present invention also provides the compounds of the formula [II']. The compounds of the formula [II'] are produced by methylating a compound of the above formula [III] wherein Y is —CN, i.e., a compound of the formula [III']:

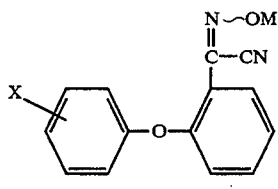

wherein X, M and — are as defined above, with a compound of the above formula [IV].

DETAILED DESCRIPTION OF THE INVENTION

In each compound disclosed in the present specification, examples of the "lower alkyl" represented by X include alkyl having 1 to 6 carbon atoms, preferably 1 to 4 carbon atoms, for example, methyl, ethyl, propyl, isopropyl, butyl, isobutyl, t-butyl and the like. Examples of the "lower alkoxy" include alkoxy having 1 to 6 carbon atoms, preferably 1 to 4 carbon atoms, for example, methoxy, ethoxy, propoxy, isopropoxy, butoxy, isobutoxy, t-butoxy and the like. Examples of "halogen" include fluorine, chlorine, bromine and iodine. Examples of the "lower alkyl" represented by R include the same groups as those described with respect to the above X. Examples of the alkali metal include potassium, sodium and the like. Examples of "halogen" represented by L include the same halogen atoms as those described with respect to the above X.

According to the process of the present invention, the compound of the formula [I] can be obtained by introducing 1 to 10 moles of methylamine gas into 1 mole of the compound of the formula [II] in a solvent such as a lower alcohol (e.g. methanol, ethanol, etc.), water, acetone, acetonitrile, benzene, toluene, methylene chloride, chloroform or the like with or without an organic base such as triethylamine, pyridine or the like, or by reacting the compound of the formula [II] with a solution of methylamine in methanol or water under normal pressure or in a sealed tube at 0° to 150° C. for 15 minutes to 24 hours.

The compound of the formula [II] can be obtained by methylating the oxime compound of the formula [III] with the compound of the formula [IV]. For example, the methylation can be conducted in a solvent such as dimethylformamide, dimethylsulfoxide, benzene, toluene, acetone, tetrahydrofuran or a mixed solvent thereof at −20° to 120° C. for 15 minutes to 5 hours in the presence of a base such as potassium carbonate, sodium carbonate, potassium hydroxide, sodium hydroxide, sodium hydride, potassium t-butoxide, sodium methylate, sodium ethylate or the like. In general, for methylation of oximes, a lot of nitron is sometimes formed depending upon-reaction conditions. However, according to this reaction, the amount of by-products is very small and the desired compound of the formula [II] is obtained in a good yield. Particularly, when the compound of the formula [III] wherein Y is —COOH is used, the desired compound which can be used for the reaction of the next step without any purification such as that by column chromatography can be obtained.

Optionally, the compound of the formula [II] can be converted into another corresponding compound of the formula [II] by a known method, for example, conversion of a nitrile into an ester.

Alternatively, the compound [I] can be directly obtained by methylating the compound of the formula [V] with the compound [IV]. This methylation can be conducted according to the same manner as that described above and the compound of the formula [I] can be obtained in a good yield without purification such as that by column chromatography.

Optionally, the compound of the formula [I] thus obtained wherein X is hydrogen can be converted into a corresponding compound of the formula [I] wherein X is lower alkyl or halogen by a known method such as alkylation or halogenation.

As described above, the compound of the formula [II'] is a novel compound and can be obtained by methylating the compound of the formula [III'] with the compound of the formula [IV] according to the same manner as that described above.

The compounds of the formulas [I] to [II] are present as E-isomer or Z-isomer, or a mixture thereof.

Regarding the compound of the formula [I], its E-isomer and Z-isomer can be represented by the following formulas:

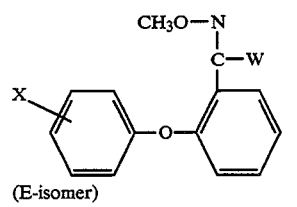

(E-isomer)

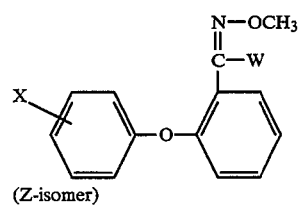

(Z-isomer)

wherein X and W are as defined above.

The compound of the formula [VI]:

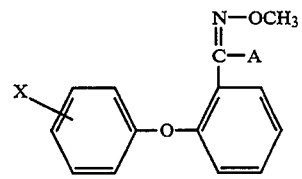

wherein A is —CONHCH$_3$ or —COOR, i.e., Z-isomer wherein W is —CONHCH$_3$ or —COOR can be converted into E-isomer of the formula [VII]:

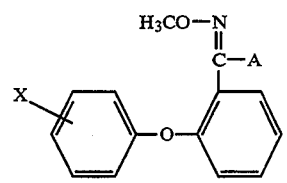

by treating it with an acid in a lower alcohol. For example, the treatment can be conducted by reacting the compound of the formula [VI] with 0.1 to 10 moles of an acid such as hydrogen chloride, hydrochloric acid, sulfuric acid or toluenesulfonic acid in a lower alcohol such as methanol, ethanol or butanol under normal pressure or in a sealed tube at 20° to 150° C. for 15 minutes to 48 hours. Further, this reaction can also be applied to a reaction mixture containing both compounds of the formulas [VI] and [VII] as well as crude products.

The compounds of the formulas [III] and [III'] which are used as starting compounds in the present invention can be produced, for example, from a known 2-phenoxyphenylacetonitrile compound (U.S. Pat. No. 4,198,418) or 2-phenoxybenzylaldehyde compound (Japanese Patent Publication No. 50204/1983) as described in the Reference Examples hereinafter. Further, the compound of the formula [IV] is known as a methylating agent.

The compound of the formula [I] thus obtained can be purified, if necessary, according to a conventional method, for example, column chromatography and can be used as a agricultural fungicide according to a known method.

As described above, according to the present invention, there is provided a novel process for producing methoxyiminoacetamide compounds which are useful as agricultural fungicides and the process of the present invention is economical with minimum by-products.

The following Examples and Reference Examples further illustrate the present invention in detail but are not to be construed to limit the scope thereof.

EXAMPLE 1

Production of 2-methoxyimino-N-methyl-2-(2-phenoxyphenyl)acetamide (mixture of E- and Z-isomers)

To α-methoxyimino-2-phenoxyphenylacetonitrile (a mixture of E- and Z-isomers) (0.50 g, 0.002 mole) were added methanol (1 ml) and 40% aqueous solution of methylamine (3.11 g, 0.01 mole) and the mixture was reacted in a sealed tube at 100° C. for 18 hours. After completion of the reaction, water was added to the reaction mixture, followed by extraction with methylene chloride. The extract was dried over anhydrous magnesium sulfate and concentrated under reduced pressure, and then the resulting residue was purified by silica gel chromatography (ethyl acetate/n-hexane) to obtain 2-methoxyimino-N-methyl-2-(2phenoxyphenyl-)acetamide (0.15 g, yield: 26.4%) as a colorless oil.

$^1$HNMR (CDCl$_3$) δppm: 2.79 (d, 1.75H, J=4.9Hz), 2.87 (d, 1.25H, J=4.9Hz), 3.91 (s, 1.75H), 4.01 (s, 1.25H), 6.32 (br, s, 0.58H), 6.64 (br, s, 0.42H), 6.85-7.61 (m, 9H)

EXAMPLE 2

Production of E-2-methoxyimino-N-methyl-2-(2-phenoxyphenyl-)acetamide

To E-α-methoxyimino-2-phenoxyphenylacetatic acid methyl ester (17.12 g, 0.06 mole) were added anhydrous methanol (60 ml) and 40% methylamine solution in methanol (13.98 g, 3.0 equivalents) and the mixture was heated under reflux for 40 minutes. After completion of the reaction, the reaction mixture was concentrated under reduced pressure and the resulting residue was purified by silica gel chromatography (ethyl acetate/n-hexane). The crystals thus obtained were recrystallized from ethyl acetate/n-hexane to obtain E-2-methoxyimino-N-methyl-2-(2-phenoxyphenyl) acetamide (12.21 g, 71.6 %) as colorless prisms (melting point: 82°-83° C.).

$^1$HNMR (CDCl$_3$) δppm: 2.87 (d, 3H, J=5.0Hz), 3.91 (s, 3H), 6.65 (br, s, 1H), 6.87-7.38 (m, 9H)

Reference Example 1

Production of E-α-methoxyimino-2-phenoxyphenylacetic acid methyl ester

To E-α-methoxyimino-2-phenoxyphenylacetonitrile (a mixture of E- and Z-isomers) (0.76 g, 0.003 mole) was added 30% hydrochloric acid in methanol (4.5 ml) and the mixture was stirred under reflux for 22 hours. After completion of the reaction, 8% aqueous solution of sodium bicarbonate (100 ml) was added to the reaction mixture and extracted with methylene chloride. The extract was dried over anhydrous magnesium sulfate and concentrated under reduced pressure. The resulting residue was purified by silica gel chromatography (ethyl acetate/n-hexane) to obtain E-α-methoxyimino-2-phenoxyphenylacetic acid methyl ester (0.40 g, 46.7%) as colorless crystals (melting point: 109°-110° C.).

$^1$HNMR (CDCl$_3$) δppm: 3.78 (s, 3H), 4.03 (s, 3H), 6.86-7.48 (m, 9H)

EXAMPLE 3

Production of E-α-methoxyimino-2-phenoxyphenylacetic acid methyl ester

To a solution of E-α-hydroxyimino-2-pheoxyphenylacetic acid (10.00 g, 0.0389 mole) in dimethyl sulfoxide (50 ml) and toluene (50 ml) was added sodium methoxide (4.83 g, 0.0894 mole) with stirring under ice cooling, and the mixture was stirred at room temperature for 20 minutes and then cooled. Dimethylsulfate (11.28 g, 0.0894 mole) was added at 6°-18° C. over 6 minutes, followed by stirring at room temperature for 4.5 hours. After completion of the reaction, conc. hydrochloric acid (1.2 ml) and water (100 ml) were added to the reaction mixture with stirring under ice cooling, followed by extraction with toluene. The extract was washed with water and concentrated under reduced pressure, and then the resulting residue was recrystallized (methanol) to obtain E-α-methoxyimino-2-phenoxyphenylacetic acid methyl ester (8.11 g, yield: 73.1%) as colorless crystals (melting point: 107°-109° C.).

$^1$HNMR (CDCl$_3$) δppm: 3.78 (s, 3H), 4.03 (s, 3H), 6.86-7.46 (m, 9H)

EXAMPLE 4

Production of E-α-methoxyimino-2-phenoxyphenylacetic acid methyl ester

To E-α-hydroxyimino-2-pheoxuphenylacetic acid (1.29 g, 0.005 mole) were added dried dimethylformamide (10 ml) and 85% potassium hydroxide (0.73 g, 0.011 mole) and the mixture was stirred at room temperature for 15 minutes. Dried toluene (10 ml) was added to the mixture, to which was further added dropwise dimethylsulfate (1.39 g, 0.011 mole) under ice cooling. After completion of the addition, the mixture was stirred at room temperature for 1.5 hours. Then, ether (100 ml) was added, followed by washing with water three times. The ether layer was dried over anhydrous magnesium sulfate and concentrated under reduced pressure. The resulting residue was purified by silica gel chromatography (ethyl acetate/n-hexane) to obtain E-α-methoxyimino-2-phenoxyphenylacetic acid methyl ester (1.20 g, yield: 84.1%) as colorless crystals (melting point: 109°–110° C.).

¹HNMR (CDCl₃) δppm: 3.78 (s, 3H), 4.03 (s, 3H), 6.86–7.46 (m, 9H)

¹HNMR (CDCl₃) δppm: 3.78 (s, 3H), 4.03 (s, 3H), 6.86–7.46 (m, 9H)

According to the same manner as that described above, each compound was produced under the following reaction conditions with varying a base and methylating agent, respectively.

TABLE 1

| Example No. | Base (eq.) | Methylating agent (eq.) | Solvent | Reaction conditions | Yield (%) |
| --- | --- | --- | --- | --- | --- |
| 7 | 60% NaH (1.1) | Me₂SO₄ (1.2) | THF | 0° C., 60 minutes | 96.5 |
| 8 | t-BuOK (1.3) | Me₂SO₄ (1.2) | THF | 0° C., 30 minutes | 82.4 |
| 9 | KOH (1.1) | MeI (1.2) | DMF/PhMe | Room temperature, 2 hours | 66.6 |

Note:
Me: methyl; t-Bu: t-butyl; THF: tetrahydrofuran; DMF: dimethylformamide; PhMe: toluene

EXAMPLE 5

Production of E-α-methoxyimino-2-(4-methylphenoxy)phenylacetic acid methyl ester E-α-hydroxyimino-2-(4-methylphenoxy)phenylacetic acid (0.87 g, 0.32 mole) was dissolved in dried dimethylformamide (6.4 ml). To the solution was added 85% potassium hydroxide (0.51 g, 0.0077 mole). After dissolving with heating, dried toluene (6.4 ml) was added. Under ice cooling, dimethylsulfate (0.97 g, 0.0077 mole) was added dropwise and the mixture was stirred at room temperature for 1.5 hours.

After completion of the reaction, water (50 ml) containing conc. hydrochloric acid (1 ml) was added to the reaction mixture and extracted with ether (50 ml). The ether layer was washed in turn with water (50 ml) and 4% aqueous solution of sodium bicarbonate (30 ml), dried over anhydrous sodium sulfate and concentrated under reduced pressure, and then the resulting residue was purified by silica gel chromatography (ethyl acetate/n-hexane) to obtain E-α-methoxyimino-2-(4-methylphenoxy)phenylacetic acid methyl ester (0.75 g, yield: 78.1%) as a colorless oil.

¹HNMR (CDCl₃) δppm: 2.32 (s, 3H), 3.79 (s, 3H), 4.04 (s, 3H), 6.85–7.39 (m, 8H)

EXAMPLE 6

Production of E-α-methoxyimino-2-phenoxyphenylacetic acid methyl ester

To E-α-hydroxyimino-2-phenoxyphenylacetic acid methyl ester (1.09 g, 0.004 mole) were added dried dimethylformamide (6 ml) and potassium hydroxide (0.29 g, 0.0044 mole) and the mixture was stirred at room temperature for 15 minutes. Then, dried toluene (6 ml) was added to the mixture, to this was further added dropwise dimethylsulfate (0.61 g, 0.0044 mole) under ice cooling. After completion of the addition, the mixture was stirred at room temperature for 2 hours. Then, ether (100 ml) was added, followed by washing with water three times. The ether layer was dried over anhydrous magnesium sulfate and concentrated under reduced pressure. The resulting residue was purified by silica gel chromatography (ethyl acetate/n-hexane) to obtain E-α-methoxyimino-2-phenoxyphenylacetic acid methyl ester (1.20 g, yield: 80.6%) as colorless crystals (melting point: 109°–110° C.).

EXAMPLE 10

Production of E-α-methoxyimino-2-(4-methylphenoxy)phenylacetic acid methyl ester E-α-hydroxyimino-2-(4-methylphenoxy)pheylacetic acid methyl ester (0.71 g, 0.0025 mole) was dissolved in dried tetrahydrofuran (10 ml), followed by the addition of 60% sodium hydride (0.13 g, 0.033 mole). Then, the mixture was stirred at room temperature for 20 minutes and to this was added dropwise a solution of dimethylsulfate (0.44 g, 0.0035 mole) dissolved in dried THF (2.5 ml) under ice cooling, followed by stirring for 1.75 hours under ice cooling. After completion of the reaction, water was added to the reaction mixture which was adjusted to pH 1 with conc. hydrochloric acid. The mixture was extracted twice with methylene chloride, dried over anhydrous sodium sulfate and concentrated under reduced pressure. The resulting residue was purified by silica gel chromatography (ethyl acetate/n-hexane) to obtain E-α-methoxyimino-2-(4-methylphenoxy)phenylacetic acid methyl ester (0.61 g, yield: 81.3%) as a colorless oil.

¹HNMR (CDCl₃) αppm: 2.32 (s, 3H), 3.79 (s, 3H), 4.04 (s, 3H), 6.85–7.39 (m, 8H)

EXAMPLE 11

Production of α-methoxyimino-2-phenoxyphenylacetonitrile (a mixture of E- and Z-isomers)

To α-hydroxyimino-2-phenoxyphenylacetonitrile (a mixture of E- and Z-isomers) (1.19 g, 0.005 mole) were added dried dimethylformamide (10 ml) and potassium carbonate (0.90 g, 0.0065 mole), and dimethylsulfate (0.76 g, 0.006 mole) was added dropwise to the mixture under ice cooling, followed by stirring at room temperature for 1.5 hours. After completion of the reaction, ether (150 ml) was added, followed by washing twice with water (100 ml). The ether layer was dried over anhydrous magnesium sulfate and concentrated under reduced pressure, and then the resulting residue was purified by silica gel chromatography (ethyl acetate/n-hexane) to obtain α-methoxyimino-2-phenoxyphenylacetonitrile (1.13 g, yield: 89.6%) as a colorless oil.

¹HNMR (CDCl₃) δppm: 4.03 (s, 0.7H), 4.17 (s, 2.3H), 6.89–7.67 (m, 9H)

EXAMPLE 12

Production of α-methoxyimino-2-phenoxyphenylacetonitrile (a mixture of E- and Z-isomers)

To α-hydroxyimino-2-phenoxyphenylacetonitrile (a mixture of E- and Z-isomers) (1.19 g, 0.005 mole) were added dried dimethylformamide (10 ml) and potassium carbonate (0.90 g, 0.006 mole), and methyl iodide (0.78 g, 0.0055 mole) was added dropwise to the mixture under ice cooling, followed by stirring at room temperature for 4 hours. After completion of the reaction, ether (150 ml) was added, followed by washing twice with water (100 ml). The ether layer was dried over anhydrous magnesium sulfate and concentrated under reduced pressure. The resulting residue was purified by silica gel chromatography (ethyl acetate/n-hexane) to obtain α-methoxyimino-2-phenoxyphenylacetonitrile (1.06 g, yield: 84.0%) as a colorless oil.

$^1$HNMR (CDCl$_3$) δppm: 4.03 (s, 0.7H), 4.17 (s, 2.3H), 6.89–7.69 (m, 9H)

EXAMPLE 13

Production of α-methoxyimino-2-(4-chlorophenoxy)phenylacetonitrile (a mixture of E- and Z-isomers)

α-hydroxyimino-2-(4-chlorophenoxy)phenylacetonitrile (a mixture of E- and Z-isomers) (1.36 g, 0.005 mole) was dissolved in dried dimethylformamide (10 ml) and potassium carbonate (0.90 g, 0.0065 mole) was added to the mixture. Further, dimethylsulfate (0.76 g, 0,006 mole) was added to the mixture under ice cooling, followed by stirring at room temperature for 1 hour. Then, ether (150 ml) was added to the mixture, which was washed twice with water. The ether layer was dried over anhydrous magnesium sulfate and concentrated under reduced pressure, and then the resulting residue was purified by silica gel chromatography (ethyl acetate/n-hexane) to obtain α-methoxyimino-2-(4-chlorophenoxy)phenylacetonitrile (1.35 g, yield: 94.4%) as a pale yellow oil.

$^1$HNMR (CDCl$_3$) δppm: 4.02 (s, 0.69H), 4.17 (s, 2.31H), 6.90–7.68 (m, 8H)

EXAMPLE 14

Production of E-2-methoxyimino-N-methyl-2-(2-phenoxyphenyl)acetamide

To E-2-hydroxyimino-N-methyl-2-(2-phenoxyphenyl)acetamide (10.00 g, 0.037 mole) were added acetone (200 ml), potassium carbonate (15.34 g, 0.111 moles) and dimethylsulfate (9.33 g, 0.074 moles) and the mixture was stirred at room temperature for 9 hours. After completion of the reaction, the reaction mixture was filtered, washed with acetone and concentrated under reduced pressure. The oil thus obtained was dissolved in toluene (50 ml) and to this was added an aqueous 1N sodium hydroxide solution (50 ml), followed by stirring at room temperature for 30 minutes. The mixture was extracted with toluene, washed with water and concentrated, and then the resulting residue was recrystallized (methanol/water) to obtain E-2-methoxyimino-N-methyl-2-(2-phenoxyphenyl)acetamide (9.93 g, yield: 94.4%) as colorless crystals (melting point: 81.5°–83° C.).

$^1$HNMR (CDCl$_3$) δppm: 2.87 (d, 3H, J=5.0Hz}, 3.91 (s, 3H), 6.65 (br, s, 1H), 6.87–7.38 (m, 9H)

EXAMPLE 15

Production of E-2-methoxyimino-N-methyl-2-[2-(4-methylpheoxy)phenyl]acetamide

E-2-hydroxyimino-N-methyl-2-[2-(4-methylphenoxy)phenyl] acetoamide (1.00 g, 0.0035 mole) was dissolved in dried acetone (7 ml), and potassium carbonate (0.63 g, 0.0046 mole) and dimethylsulfate (0.53 g, 0.0042 mole) were added to the mixture, which was reacted at room temperature for 22 hours. After completion of the reaction, water was added to the reaction mixture, which was extracted twice with methylene chloride, dried over anhydrous sodium sulfate and concentrated under reduced pressure. The resulting residue was purified by silica gel chromatography (ethyl acetate/n-hexane) to obtain E-2-methoxyimino-N-methyl-2-[2-(4-methylphenoxy)phenyl]-acetamide as colorless crystals (0.96 g, yield: 92.3%).

$^1$HNMR (CDCl$_3$) δppm: 2.29 (s, 3H), 2.81 (d, 3H, J=4.9Hz), 3.89 (s, 3H), 6.71 (br, s, 1H), 6.82 (d, 1H, J=8.1Hz), 6.89–6.92 (m, 2H), 7.05–7.10 (m, 3H), 7.23–7.31 (m, 2H)

Reference Example 2

Production of E-2-hydroxyimino-N-methyl-2-(2-phenoxyphenyl)acetamide

To crude E-α-hydroxyimino-2-phenoxyphenylacetic acid methyl ester (39.6 g, 0.0747 mole, purity: 51.2%) were added methanol (100 ml) and 40% aqueous solution of methylamine (15.45 g, 0,199 mole) and the mixture was stirred at room temperature for 15 hours. Then, 40% aqueous solution of methylamine (7.73 g, 0.0995 mole) was added to the mixture which was stirred in an oil bath at 70° C. for 6 hours. After completion of the reaction, water (200 ml) and toluene (100 ml) were added to the reaction mixture, which was stirred with ice cooling for one hour. The precipitated crystals were filtered off and recrystallized (methanol/toluene) to obtain E-2-hydroxyimino-N-methyl-2-(2-phenoxyphenyl)acetamide (12.31 g, yield: 60.1%) as colorless crystals (melting point: 183°–184.5° C.).

$^1$HNMR (d$_6$-DMSO$_4$) δppm: 2.65 (d, 3H, J=4.5Hz), 6.30–7.47 (m, 9H), 7.92 (q, 1H, J=4.5Hz)

Reference Example 3

Production of E-2-hydroxyimino-N-methyl-2-[2-(4-methylphenoxy)phenyl]acetamide

E-α-hydroxyimino-2-(4-methylphenoxy)phenylacetic acid methyl ester (1.00 g, 0.0035 mole) was dissolved in methanol (7 ml) and 40% methylamine solution in methanol (0.54 g, 0.007 mole) was added to the mixture, which was refluxed for 70 minutes. A 40% methylamine solution in methanol (1.36 g, 0.0175 mole) was further added to the mixture, which was refluxed for 3 hours. After completion of the reaction, the reaction mixture was concentrated under reduced pressure to give E-2-hydroxyimino-N-methyl-2-[2-(4-methylphenoxy)phenyl]acetamide (1.00 g, yield: 100.0%) as an amorphous.

$^1$HNMR (CDCl$_3$) δppm: 2.31 (s, 3H), 2.86 (d, 3H, J=5.9Hz), 6.60 (br, s, 1H), 6.84–7.36 (m, 8H), 7.93 (br, s, 1H).

Reference Example 4

Production of
E-α-hydroxyimino-2-phenoxyphenylacetic acid

To E-α-hydroxyimino-2-phenoxyphenylacetic acid methyl ester (9.99 g, 0.0368 mole) were added methanol (36.8 ml), sodium hydroxide (3.23 g, 0.081 mole) and water (36.8 ml) and the mixture was heated under reflux for one hour. After heating, conc. hydrochloric acid (1 ml) was added to the mixture under ice cooling and the precipitated crystals were filtered off and recrystallized (methanol/ethyl acetate/n-hexane) to obtain E-α-hydroxyimino-2-phenoxyphenylacetic acid (6.90 g, yield: 72.9%) as colorless crystals (decomposition: 180° C.).

$^1$HNMR (d-DMSO$_4$) δppm: 6.83–7.38 (m, 9H), 12.26 (br, s, 1H), 12.85 (br, s, 1H)

Reference Example 5

Production of
E-α-hydroxyimino-2-(4-methylphenoxy)phenylacetic acid

To E-α-hydroxyimino-2-(4-methylphenoxy)phenylacetic acid methyl ester (1.00 g, 0.0035 mole) were added methanol (3.5 ml), water (3.5 ml), sodium hydroxide (0.31 g, 0.0077 mole) and the mixture was heated under reflux for one hour. After cooling to room temperature, the resultant was adjusted to pH 1 with 5% of hydrochloric acid. After stirring at room temperature, the crystals were filtered off and washed with water to obtain colorless crystals of E-α-hydroxyimino-2-(4-methylphenoxy)phenylacetic acid (0.90 g, yield: 94.7%).

$^1$HNMR (d$_6$-DMSO$_4$) δppm: 2.27 (s, 3H), 6.78–7.37 (m, 8H)

Reference Example 6

Production of
α-hydroxyimino-2-phenoxyphenylacetonitrile (a mixture of E- and Z-isomers)

To anhydrous ethanol (15 ml) was dissolved sodium (0.55 g, 0.024 mole) and a mixture of 2-phenoxyphenylacetonitrile (4.18 g, 0.02 mole) and anhydrous ethanol (3 ml) was added dropwise to the mixture below 0° C. over 7 minutes. Isoamyl nitrite (3.51 g, 0.03 mole) was further added dropwise to the mixture below 0° C. over 10 minutes, followed by stirring at room temperature for 24 hours. After completion of the reaction, 5% hydrochloric acid was added to the reaction mixture, which was extracted with ether and dried over anhydrous magnesium sulfate. The crude product obtained by concentration under reduced pressure was purified by silica gel chromatography (ethyl acetate/n-hexane) to obtain α-hydroxyimino-2-phenoxyphenylacetonitrile (4.53 g, yield: 95.1%) as crystals having a low melting temperature.

$^1$HNMR (CDCl$_3$) δppm: 6.83–7.67 (m, 9H), 8.68 (br, s, 0.25H), 9.02 (br, s, 0.75H)

Reference Example 7

Production of
α-hydroxyimino-2-(4-chlorophenoxy)phenylacetonitrile (a mixture of E-and Z-isomers)

To anhydrous ethanol (25 ml) was added metallic sodium (0.97 g, 0.042 mole), and after dissolution, a solution of 2-(4-chlorophenoxy)phenylacetonitrile (8.53 g, 0.035 mole) in anhydrous ethanol (7 ml) was added dropwise to the mixture. Then, isoamyl nitrite (6.15 g, 0.0525 mole) was added dropwise to the mixture. After reaction at room temperature for 2.5 hours, water was added to the reaction mixture, which was adjusted to pH 1 with conc. hydrochloric acid, extracted with ether, washed with water and dried over anhydrous magnesium sulfate.

Ether was concentrated under reduced pressure and the resulting residue was purified by silica gel chromatography (ethyl acetate/n-hexane) to obtain α-hydroxyimino-2-(4-chlorophenoxy)phenylacetonitrile (9.03 g, yield: 94.6%) as a light brown viscous liquid.

$^1$HNMR (CDCl$_3$) δppm: 6.90–7.68 (m, 8H), 9.12 (br, s, 0.28H), 9.46 (br, s, 0.72H)

Reference Example 8

Production of
E-α-hydroxyimino-2-phenoxyphenylacetic acid

To α-hydroxyimino-2-phenoxyphenylacetonitrile (a mixture of E- and Z-isomers) (0.71 g, 0,003 mole) were added ethanol (3 ml), potassium hydroxide (0.40 g, 0.0072 mole) and water (3 ml). After completion of the reaction, methylene chloride (10 ml) and 10% hydrochloric acid were added to the reaction mixture, and the crystals of α-hydroxyimino-2-phenoxyphenylacetic acid precipitated were filtered off to obtain colorless crystals (0.47 g, yield: 60.9 %).

$^1$HNMR (d$_6$-DMSO$_4$) δppm: 6.83–7.38 (m, 9H), 12.26 (br, s, 1H), 12.85 (br, s, 1H)

Reference Example 9

Production of 2-phenoxybenzaldoxime

To 2-phenoxybenzaldehyde (4.96 g, 0.025 mole) were added anhydrous methanol (50 ml) and hydroxylamine hydrochloride (2.08 g, 0.03 mole), and the mixture was stirred at 60° C. for 3 hours. After completion of the reaction, water (200 ml) was added to the reaction mixture, which was extracted with methylene chloride and dried over magnesium sulfate. The crude product obtained by concentration under reduced pressure was purified by silica gel chromatography (ethyl acetate/n-hexane) to obtain 2-phenoxybenzaldoxime (3.95 g, yield: 74.1%) as a colorless oil.

$^1$HNMR (CDCl$_3$) δppm: 6.88–7.41 (m, 8H), 7.45 (s, 1H), 7.86 (dd, 1H, J=7.9., 2.0), 8.49 (s, 1H)

EXAMPLE 16

Production of
α-methoxyimino-2-phenoxyphenylacetonitrile (a mixture of E- and Z-isomers)

To 2-phenoxybenzaldoxime (1.07 g, 0,005 mole) was added dried ether (10 ml), and chlorine (0.46 g, 0.0065 mole) was introduced into the mixture below −10° C., followed by stirring at 0° C. for 5 hours. After the completion of the reaction, the reaction mixture was concentrated under reduced pressure, and then, dried methylene chloride (10 ml) and tetraethylammonium cyanide (0.86 g, 0.0055 mole) were added to the resulting residue and the mixture was stirred overnight. After completion of the reaction, water (150 ml) was added to the reaction mixture, which was extracted with methylene chloride, dried over anhydrous magnesium sulfate and purified by silica gel chromatography (ethyl acetate/n-hexane) to obtain crude α-hydroxyimino-2-phenoxyphenylacetnitrile (0.51 g), to which were added dried dimethylformamide (4 ml) and potassium carbonate (0.36 g, 0.0026 mole). Dimethyl sulfate (0.30 g, 0.0024 mole) was further added to the mixture, which was stirred at room temperature for 2 hours. After completion of the reaction, ether (100 ml) was added to the reaction mixture, which was washed twice with water, dried over anhydrous magnesium sulfate and concentrated under reduced pressure. The crude product thus obtained was purified by silica gel chromatography (ethyl acetate/n-hexane) to obtain α-methoxyimino-2-phenoxyphenylacetnitrile (0.21 g, yield: 16.6%) as a colorless oil.

$^1$HNMR (CDCl$_3$) δppm: 4.03 (s, 0.7H), 4.17 (s, 2.3H), 6.89–7.67 (m, 9H)

EXAMPLE 17

Production of E-α-methoxyimino-2-phenoxyphenylacetic acid methyl ester

To 1.62 M solution of n-butyllithium in hexane (500 ml, 0.81 mole) were added dropwise a mixture of diphenyl ether (206.81 g, 1,215 moles) and dried tetrahydrofuran (405 ml) below 5° C. over 40 minutes and the mixture was stirred at room temperature for 24 hours. After completion of the reaction, the reaction mixture was added dropwise to a stirring solution of dimethyl oxalate (118.09 g, 1,215 moles) in dried tetrahydrofuran (810 ml) below 0° C. over 50 minutes, followed by stirring at room temperature for 24 hours.

After completion of the reaction, ice-water (2 liters) was added to the mixture, which was extracted with toluene (500 ml) and the extract was washed with water. Then, the solution was dried over anhydrous sodium sulfate and concentrated under reduced pressure to obtain a brown oil (302.94 g). To this oil were added methanol (1.3 liters) and hydroxylamine hydrochloride (47.25 g, 0.68 mole) and the mixture was heated under. reflux for one hour, and then, a solution of sodium hydroxide (79.2 g, 1.98 moles) in water (450 ml) was further added to the mixture, which was heated under reflux for one hour. After completion of the reaction, methanol was distilled off under reduced pressure, followed by the addition of water (1.8 liters) and further washing twice with methylene chloride (1 liter). Then, conc. hydrochloric acid was added to the aqueous layer until pH became lower than 2 and the crystals precipitated were filtered off to obtain crude crystals of E-α-hydroxyimino-2-phenoxyphenylacetic acid (141.55 g, yield: 68.0% from n-butyllithium). To the crude crystals (25.73 g, 0.1 mole) thus obtained were added dried dimethylformamide (150 ml) and 85 % potassium hydroxide (14.52 g, 0.22 mole), and the mixture was heated to obtain a solution. Then, dried toluene was added to the solution, and dimethyl sulfate (27.75 g, 0.22 moles) was added dropwise at 25° to 30° C. over 5 minutes and the mixture was stirred at room temperature for 1.5 hours. After completion of the reaction, 1% hydrochloric acid (700 ml) was added to the reaction mixture, which was extracted with toluene (500 ml), and then, the extract was washed with an aqueous 2% sodium bicarbonate solution and dried over anhydrous sodium sulfate. The crude product obtained by concentration under reduced pressure was purified by recrystallization (methanol) to obtain E-α-methoxyimino-2-phenoxyphenylacetic acid methyl ester (21.15 g, yield: 74.1%) as colorless crystals (melting point: 109°–110° C.).

$^1$HNMR (CDCl$_3$) δppm: 3.78 (s, 3H), 4.03 (s, 3H), 6.86–7.46 (m, 9H)

EXAMPLE 18

Production of E-α-methoxyimino-2-phenoxyphenylacetic acid methyl ester

To Z-α-methoxyimino-2-phenoxyphenylacetic acid methyl ester VI′(0.29 g, 1.0 mmole) were added dried methanol (3 ml) and 10% hydrochloric acid solution in methanol (0.36 g, 1.0 mmole) and the mixture was heated under reflux for 6 hours to conduct isomerization.

The reaction mixture was concentrated under reduced pressure, giving a crystalline residue(0.29g). The residue consists of E-isomer and Z-isomer in the ratio of 77.6:22.4, by a $^1$H-NMR measurement.

EXAMPLE 19

Production of E-2-methoxyimino-N-methyl-2-(2-phenoxyphenyl)acetamide

To Z-2-methoxyimino-N-methyl-2-(2phenoxyphenyl)acetamide VI″ (0.28 g, 1.0 mmole) were added dried methanol (3 ml) and 10% hydrochloric acid solution in methanol (0.36 g, 1.0 mmole) and the mixture was heated under reflux for 6 hours to conduct isomerization.

The reaction mixture was concentrated under reduced pressure, giving a crystalline residue (0.28 g). The residue consists of E-isomer and Z-isomer in the ratio of 91.5:8.5, by a $^1$H-NMR measurement.

EXAMPLE 20

Production of E-2-methoxyimino-N-methyl-2-(2-phenoxyphenyl)acetamide

To Z-2-methoxyimino-N-methyl-2-(2-phenoxyphenyl)acetamide VI″ (0.42 g, 1.48 mmol) were added n-butanol (4.4 ml) and conc. hydrochloric acid (0.46 g, 4.44 mmol) and the mixture was heated at 80° C. for 3 hours to conduct isomerization.

The reaction mixture was concentrated under reduced pressure, giving a crystalline residue consists of E-isomer and Z-isomer in the ratio of 90:10, by a H$^1$-NMR measurement.

What is claimed is:

1. A process for producing a E-isomer of the formula:

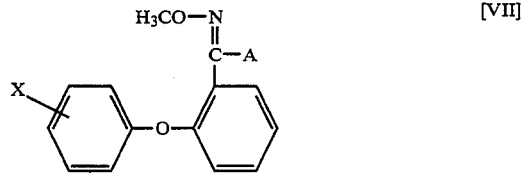

[VII]

wherein X is hydrogen, lower alkyl, lower alkoxy or halogen; A is —CONHCH$_3$ or —COOR; and R is lower alkyl, which comprises reacting a Z-isomer of the formula [VI]:

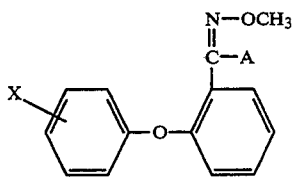

[VI]

wherein X, A and R are as defined above, with hydrogen chloride, hydrochloric acid, sulfuric acid or toluenesulfonic acid in methanol, ethanol or butanol under normal pressure or in a sealed tube at 20° to 150° C.

2. A process according to claim 1, wherein the compound [VI] is reacted with hydrogen chloride, hydrochloric acid, sulfuric acid or toluenesulfonic acid in methanol, ethanol or butanol under normal pressure or in a sealed tube at 20° to 150° C. for 15 minutes to 48 hours.

3. A process according to claim 1, wherein the reaction of the Z-isomer of the formula [VI] is conducted in a reaction mixture also containing the compound of the formula [VII].

* * * * *